United States Patent
Antons et al.

(10) Patent No.: US 11,161,840 B2
(45) Date of Patent: Nov. 2, 2021

(54) PROCESS FOR PRODUCING HETEROCYLIC COMPOUNDS

(71) Applicant: Bayer CropScience Aktiengesellschaft, Monheim am Rhein (DE)

(72) Inventors: Stefan Antons, Leverkusen (DE); Martin Littmann, Leverkusen (DE); Joerg Schulz, Dormagen (DE); Wahed Ahmed Moradi, Monheim (DE); Thomas Geller, Odenthal (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 459 days.

(21) Appl. No.: 16/306,180

(22) PCT Filed: May 26, 2017

(86) PCT No.: PCT/EP2017/062731
§ 371 (c)(1),
(2) Date: Nov. 30, 2018

(87) PCT Pub. No.: WO2017/211594
PCT Pub. Date: Dec. 14, 2017

(65) Prior Publication Data
US 2021/0261536 A1    Aug. 26, 2021

(30) Foreign Application Priority Data

Jun. 6, 2016 (EP) .................................. 16173126

(51) Int. Cl.
*C07D 417/06*    (2006.01)

(52) U.S. Cl.
CPC .................. *C07D 417/06* (2013.01)

(58) Field of Classification Search
CPC .................................................. C07D 417/06
See application file for complete search history.

(56) References Cited

U.S. PATENT DOCUMENTS

| | | |
|---|---|---|
| 4,803,277 A | 2/1989 | Shiokawa et al. |
| 4,849,432 A | 7/1989 | Shiokawa et al. |
| 4,882,344 A | 11/1989 | Shiokawa et al. |
| 4,988,712 A | 1/1991 | Shiokawa et al. |
| 6,211,379 B1 | 4/2001 | Seifert et al. |
| 6,667,401 B2 | 12/2003 | Seifert et al. |
| 2019/0152933 A1 | 5/2019 | Kulkarni et al. |
| 2020/0347024 A1 | 11/2020 | Kulkarni et al. |

FOREIGN PATENT DOCUMENTS

| | | |
|---|---|---|
| CN | 1401646 A | 3/2003 |
| EP | 0235725 A2 | 9/1987 |
| EP | 0235752 A2 | 9/1987 |
| EP | 0259738 A2 | 3/1988 |
| EP | 1024140 A1 | 8/2000 |
| EP | 1252159 A1 | 10/2002 |
| WO | 01/53296 A1 | 7/2001 |
| WO | 2017048628 A1 | 3/2017 |

OTHER PUBLICATIONS

PCT International Search Report for PCT/EP2017/062731, dated Jul. 31, 2017.

*Primary Examiner* — Kamal A Saeed
(74) *Attorney, Agent, or Firm* — McBee Moore & Vanik IP, LLC

(57) ABSTRACT

The present invention relates to a process for producing compounds of formula (I)

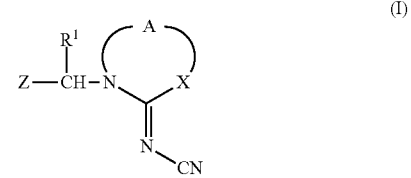

in which $R^1$, A, X and Z are as defined in the description by reaction of compounds of formula (II)

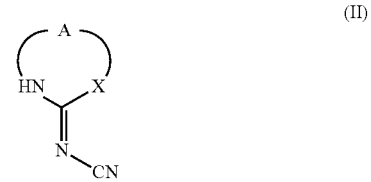

or salts thereof with 2-chloro-5-chloromethylpyridine in a nonpolar aliphatic or aromatic solvent, preferably in the presence of a phase transfer catalyst.

13 Claims, No Drawings

PROCESS FOR PRODUCING HETEROCYLIC COMPOUNDS

CROSS-REFERENCE TO RELATED APPLICATIONS

This application is a National Stage entry of International Application No. PCT/EP2017/062731, filed May 26, 2017, which claims priority to European Patent Application No. 16173126.0, filed Jun. 6, 2016.

BACKGROUND

Field

The present invention relates to a novel process for producing known heterocyclic compounds of formula I.

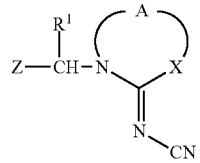
(I)

Description of Related Art

The production of unsaturated, heterocyclic compounds by alkylation of unsubstituted ring-member atoms which may be performed inter alia in alcohol (EP 0 259 738) or in only partially water-miscible alcohols (and EP1 252 159) is known.

EP 1024140 describes the reaction of compounds of formula (II)

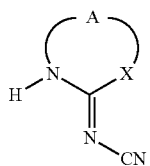
(II)

with 2-chloro-5-chloromethylpyridine in the presence of protic solvents

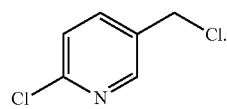

Protic solvents proposed include in particular alcohols. The addition of phase transfer catalysts such as tetrabutylammonium bromide is also mentioned. However, reported example 2 (page 5) in EP 1024140 achieves only 72% of theory of the product which is much too low for a process on a large industrial scale.

Thus, in all these cases the yield achieved is only unsatisfactory. A subsequent purification of the product is therefore necessary to achieve sufficient purity and therefore very costly.

There is therefore an urgent need for an improved process which makes it possible to produce the desired product of formula I in an industrially easily performable manner but higher yields.

SUMMARY

One aspect of the present invention relates to a process for producing compounds of formula (I)

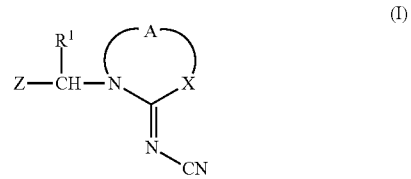
(I)

in which $R^1$ stands for a hydrogen atom or an alkyl group, preferably a $C_1$-$C_4$-alkyl group, A stands for an ethylene group which may be substituted by alkyl, preferably $C_1$-$C_4$-alkyl, or a trimethylene group which may be substituted by alkyl, preferably $C_1$-$C_4$-alkyl, X stands for an oxygen or sulfur atom or the groups

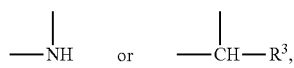

in which $R^3$ stands for a hydrogen atom or an alkyl group, preferably a $C_1$-$C_4$-alkyl group, and Z describes an optionally substituted 5- or 6-membered heterocyclic group comprising at least two heteroatoms selected from oxygen, sulfur and nitrogen atoms or an optionally substituted 3- or 4-pyridyl group, characterized in that compounds of formula (II)

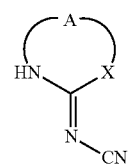
(II)

or the salts thereof of formula (IIa),

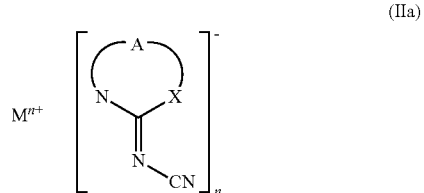
(IIa)

in which

A and X are as defined above, depending on the counterion ($M^{n+}$) n may be one or two, $M^{n+}$ represents ammonium (n=1), alkali metal (n=1) or alkaline earth metal cation (n=2), in a nonpolar aliphatic or aromatic organic solvent in the presence of a phase transfer catalyst, preferably an ammonium salt, more preferably a quaternary ammonium salt, are reacted with 2-chloro-5-chloromethylpyridine.

DETAILED DESCRIPTION OF A PREFERRED EMBODIMENT

One preferred embodiment relates to a process according to the invention, wherein the phase transfer catalyst is an ammonium salt of formula

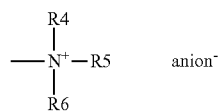

wherein R4,R5,R6 stand for hydrogen or a $C_1$-$C_{12}$-alkyl group or -benzyl or -alkylbenzyl, preferably for a $C_1$-$C_{12}$-alkyl group (for the avoidance of doubt, —N in (—NR4R5R6)$^+$ is the familiar shorthand for a methyl group, (—NR4R5R6)$^+$ is the shorthand for (Me-NR4R5R6)$^+$), and anion$^-$ stands for OH, chloride, bromide, iodide or cyanide;

or

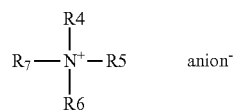

wherein R4, R5, R6 stand for hydrogen or a $C_1$-$C_{12}$-alkyl group or -benzyl or -alkylbenzyl (preferably $C_1$-$C_{12}$-alkylbenzyl) and R$_7$ stands for a $C_1$-$C_{12}$-alkyl group or -benzyl or -alkylbenzyl, preferably for a $C_1$-$C_{12}$-alkyl group, and anion$^-$ stands for OH, chloride, bromide, iodide or cyanide, preferably for chloride.

One preferred embodiment relates to a process according to the invention, where the organically soluble quaternary ammonium salt is aliquat 336 (methyl-tri-n-octylammonium chloride).

One preferred embodiment relates to a process according to the invention in which the solvent is selected from benzene, toluene, xylene, mixtures thereof or hexane, cyclohexane, methylcyclohexane and mixtures thereof.

One preferred embodiment relates to a process according to the invention, wherein the solvent is toluene.

One preferred embodiment relates to a process according to the invention, wherein M$^+$ is an Na$^+$ ion.

One preferred embodiment relates to a process according to the invention, wherein the compound of formula (I) is the compound of formula (Ia)

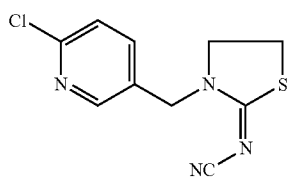

characterized in that compounds of formula (IIb)

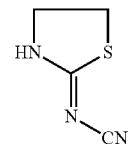

in the presence of a base, preferably NaOH,
or the salts thereof of formula (IIc),

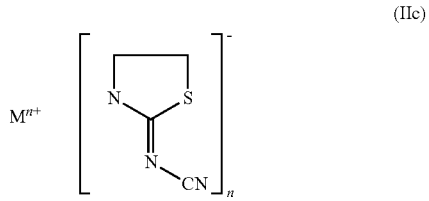

wherein depending on the counterion $M^{n+}$ n is one or two and $M^{n+}$ is an ammonium (n=1), an alkali metal (n=1) or an alkaline earth metal cation (n=2), preferably a Na$^+$ ion, in the presence of a phase transfer catalyst as described herein are reacted with 2-chloro-5-chloromethylpyridine.

It is apparent to those skilled in the art that all embodiments described herein may be combined with one another but it will be appreciated that combinations contrary to the laws of physics are excluded.

It has now been found that, surprisingly, it is precisely the use of nonpolar solvents such as aliphatic or aromatic hydrocarbons and the use of a suitable phase transfer catalyst that can achieve a markedly better yield.

Compounds of Formula (I)

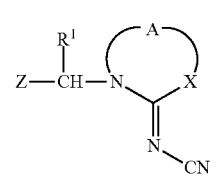

where

R$^1$ stands for a hydrogen atom or an alkyl group, preferably a $C_1$-$C_4$-alkyl group, A stands for an ethylene group which may be substituted by alkyl, preferably by a $C_1$-$C_4$-alkyl, or a trimethylene group which may be substituted by alkyl, preferably by a $C_1$-$C_4$-alkyl, X stands for an oxygen or sulfur atom or the groups

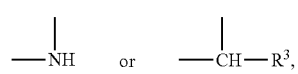

in which

R$^3$ stands for a hydrogen atom or an alkyl group, preferably a $C_1$-$C_4$-alkyl group, and Z describes an optionally substituted 5- or 6-membered heterocyclic group comprising at least two heteroatoms selected from oxygen, sulfur and nitrogen atoms or an optionally substituted 3- or 4-pyridyl group, are obtained when compounds of formula (II)

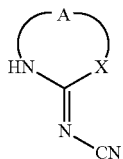
(II)

or ammonium, alkali metal or alkaline earth metal salts of the compound of formula IIa

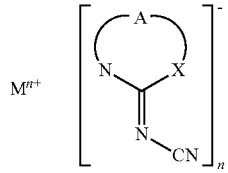
(IIa)

in which depending on the counterion ($M^{n+}$) n may be one or two, $M^{n+}$ may be ammonium (n=1), alkali metal (n=1) or alkaline earth metal cation (n=2) and A and X are as defined above, in the presence of an organically soluble phase transfer catalyst are reacted with 2-chloro-5-chloromethylpyridine of formula (III).

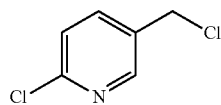
(III)

Surprisingly, the process according to the invention makes it possible to produce the abovementioned compounds in a simpler manner, i.e. in a smaller number of process steps and in substantially better yields.

In one preferred embodiment in general formulae (I) and (II) and (IIa) the variables (provided they appear in one of the three formulae) are as follows $R^1$ preferably stands for hydrogen or a $C_1$-$C_3$-alkyl group, particularly preferably for hydrogen;

A preferably stands for an ethylene or trimethylene group which may each be substituted by a $C_1$-$C_3$-alkyl group, particularly preferably for an ethylene group;

X preferably stands for an oxygen or sulfur atom or for the group

particularly preferably for an oxygen atom or the group

Z preferably stands for a halogenated 5- or 6-membered heterocyclic group which comprises 2 heteroatoms selected from the group oxygen, sulfur and nitrogen or for a halogenated 3- or 4-pyridyl group, particularly preferably for a halogenated thiazolyl or 3-pyridyl group, very particularly preferably for 2-chloro-pyrid-5-yl.

A very particularly preferred embodiment is directed to a process for producing a compound of formula (Ia),

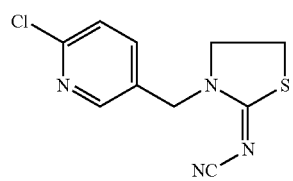
(Ia)

which is obtained by reacting the compound of formula (IIb)

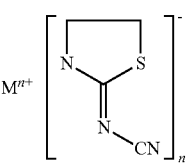
(IIb)

with an inorganic base and in the presence of a nonpolar aliphatic or aromatic organic solvent, preferably an aromatic hydrocarbon such as toluene or xylene, and by subsequent reaction with 2-chloro-5-chloromethylpyridine, particularly preferably wherein the reaction is carried out in the presence of a phase transfer catalyst, or which is obtained by reacting the compound of formula (IIc)

(IIc)

wherein depending on the counterion $M^{n+}$ n is 1 or two and $M^{n+}$ is an ammonium (n=1), an alkali metal (n=1) or an alkaline earth metal cation (n=2), preferably a $Na^+$ ion.

Preferred inorganic bases are ammonium-containing bases or aqueous alkali metal or alkaline earth metal hydroxide solutions; particular preference is given to NaOH.

Solvents which may be employed include all nonpolar aliphatic or aromatic solvents or mixtures thereof.

Aromatic solvents used by way of example include:
benzene, toluene or xylene or mixtures thereof;
hexane, cyclohexane, methylcyclohexane or mixtures thereof;
and mixtures of aliphatic and aromatic solvents.
Particular preference is given to toluene.
To improve conversions and yields, phase transfer catalysts are additionally used such as for example

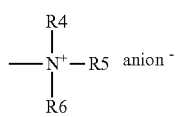

wherein R4,R5,R6 stand for hydrogen or a $C_1$-$C_{12}$-alkyl group or -benzyl or -alkylbenzyl (methyl-N(R4, R5, R6)$^+$ anion$^-$,
or

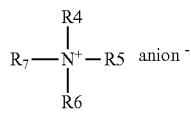

wherein R4, R5, R6 stand for hydrogen or a $C_1$-$C_{12}$-alkyl group or -benzyl or -alkylbenzyl and $R_7$ stands for a $C_1$-$C_{12}$-alkyl group or -benzyl or -alkylbenzyl, preferably for a $C_1$-$C_{12}$-alkyl group, IIa and anion$^-$ stands for OH, chloride, bromide, iodide, or cyanide, particularly preferably for chloride.

Especially preferred phase transfer catalysts are organically soluble quaternary ammonium salts, particularly preferably quaternary $C_1$-$C_{12}$-alkylammonium halogen salts, particularly preferably t $C_1$-$C_{12}$-alkylammonium chloride salts such as Aliquat 336 (methyl-tri-n-octylammonium chloride).

When water is present the process is performed in a pH range between 6 and 14. It is preferable when the range is between pH 10 and pH 13.

The reaction may be performed at temperatures from 10° C. to 130° C. such as 15° C. to 130° C., optionally under vacuum or under pressure. 40° C. to 80° C. is preferred.

The reaction is advantageously performed under atmospheric pressure but it is also possible to work under reduced or elevated pressure.

Performing the process in practice involves for example reacting 1 mol of 2-chloro-5-chloromethylpyridine with 0.95 to 3 mol of the compounds of formula (II), preferably 1.0 to approximately 2.5 mol, in a solvent such as toluene, preferably in the presence of a catalyst such as a methytri-octylammonium chloride (Aliquat 336).

When using water in a biphasic system the process is preferably operated at pH 8-13.

The reaction time is between 0.1 and 12 hours, preferably 1 to 5 hours.

Once the reaction is complete the product may be isolated by simple cooling below the reaction temperature, for example to 10° C. or less, such as in the range from −10° C. to 10° C., in the range from 0° C. to 10° C. or below 10° C. such as in the range from 0° C. to 9° C., and filtration.

It is alternatively possible to initially separate the phases. Separation of the organic phase is effected at 50° C. to 120° C., preferably at 40° C. to 80° C. The mixture is then cooled as described above and the precipitated active substance is isolated, washed and optionally recrystallized.

The compounds of formula (I) are suitable for use as insecticides for example (EP A2 0235 752, EP A2 0259 738).

The examples which follow illustrate the subject matter of the invention without limiting it in any way.

Example 1

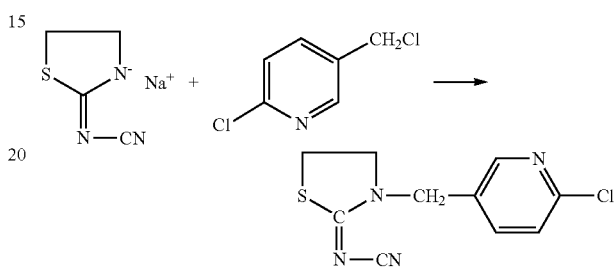

0.501 mol of CCMP (2-chloro-5-chloromethylpyridine) were initially charged in 260 g of toluene together with 5 g of aliquat 336 (methyl-tri-n-octylammonium chloride) and heated to 70° C. Over 1 h, 250 g of a 29.8% strength solution of 2-cyaniminothiazolidine sodium salt (0.5 mol) in water were metered in. Stirring was then continued until complete conversion of the cyaniminothiazolidine. The batch was then cooled to 10° C. and filtered.

The obtained solid was then washed twice with respective 70 g portions of toluene chilled to 10° C. After drying under vacuum 119 g of the 98.5% pure active substance were thus obtained (92.5% of theory, smp 136-137° C.).

Example 2

12 mol of CCMP (2-chloro-5-chloromethylpyridine) were initially charged in 1207 g of toluene together with 71 g of aliquat 336 (methyl-tri-n-octylammonium chloride) and heated to 60° C. Over 2 h, 11.6 mol of a 29.8% strength solution of 2-cyaniminothiazolidine sodium salt in water were metered in. Stirring was then continued until complete conversion of the cyaniminothiazolidine. The batch was then cooled to 10° C. and filtered.

The obtained solid was then washed once with 1600 g of toluene chilled to 10° C. and 2000 g of water. After drying under vacuum 2820 g of the 99.8% pure active substance were thus obtained (95% of theory).

Example 3

Comparison in Butanol Instead of Toluene

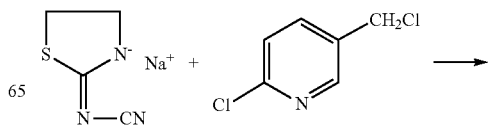

-continued

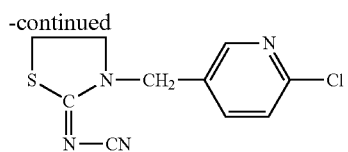

0.501 mol of CCMP (2-chloro-5-chloromethylpyridine) were initially charged in 260 g of 1-butanol together with 5 g of aliquat 336 (methyl-tri-n-octylammonium chloride) and heated to 70° C. Over one hour, 250 g of a 29.8% strength solution of 2-cyaniminothiazolidine sodium salt (0.5 mol) in water were metered in. Stirring was then continued until complete conversion of the cyaniminothiazolidine. The batch was then cooled to 10° C. and filtered.

The obtained solid was then washed twice with respective 70 g portions of 1-butanol/toluene (1:1 mixture) chilled to 10° C. After drying under vacuum 88.1 g of the 97.8% pure active substance were thus obtained (68.2% of theory).

Example 4

EP 11024140 Comparison 0.615 mol of potassium carbonate and 0.3 mol of 2-cyaniminothiazolidine were suspended in 100 ml of n-butanol and stirred at 60° C. for 1 h. Over 2 h, at 70° C., 0.315 mol of 2-chloro-5-chloromethylpyridine/2-chloro-5-methylpyridine (CCMP/CMP, 23% CCMP in the mixture) suspended in 100 ml of n-butanol were added and stirred for 2 h at 72° C. After cooling to 65° C., 400 g of water were then added and the phases separated. The organic phase was then stirred for 3 h at 50° C. and then stirred for 18 h at 5° C. Precipitated product was filtered off and dried; 59.6 g (78% of theory).

Example 4

EP 11024140 Comparison with Phase Transfer Catalyst 0.3 mol of 2-cyaniminothiazolidine and 4.2 g of tetrabutylammonium bromide were suspended in 300 ml of water and heated to 70° C. This was followed by addition of 0.315 mol of CMP/CCMP mixture. The pH of the reaction mixture was continuously held with NaOH at 8 to 8.5. After 2 hours of reaction time at 60° C. a phase separation was then performed at this temperature and the organic phase was diluted with 150 ml of butanol and stirred. The mixture was cooled to 3° C. over 3 h and precipitated product suctioned off; 58.5 g (76% of theory) were thus obtained.

The invention claimed is:

1. A process for producing a compound of formula (I)

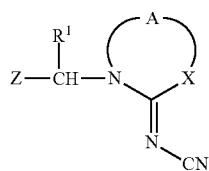

in which
R$^1$ stands for a hydrogen atom,
A stands for an ethylene group which may be substituted by alkyl, or a trimethylene group which may be substituted by alkyl,
X stands for an oxygen or sulfur atom or the groups

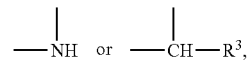

in which
R$^3$ stands for a hydrogen atom or an alkyl group, and
Z is 2-chloro-5-pyridinyl,
said process comprising reacting one or more compounds of formula (II)

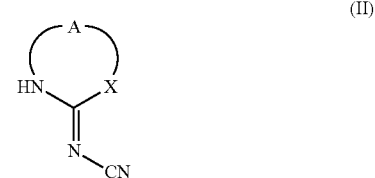

or salts thereof of formula (IIa),

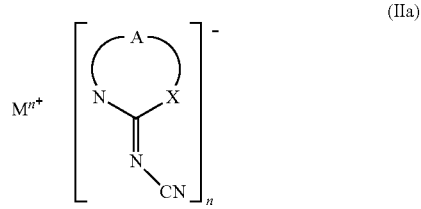

in which
A and X are as defined above,
depending on the counterion (M$^{n+}$) n may be one or two,
M$^{n+}$ represents ammonium (n=1), alkali metal (n=1) or alkaline earth metal cation (n=2),
in a nonpolar aliphatic or aromatic organic solvent in the presence of a phase transfer catalyst,
with 2-chloro-5-chloromethylpyridine.

2. The process according to claim 1, wherein the phase transfer catalyst is an ammonium salt of formula

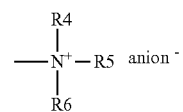

wherein R4,R5,R6 stand for hydrogen or a C$_1$-C$_{12}$-alkyl group or -benzyl or -alkylbenzyl and anion$^-$ stands for OH, chloride, bromide, iodide or cyanide;
or

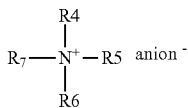

wherein R4, R5, R6 stand for hydrogen or a $C_1$-$C_{12}$-alkyl group or -benzyl or -alkylbenzyl and $R_7$ stands for a $C_1$-$C_{12}$-alkyl group or -benzyl or -alkylbenzyl, and anion⁻ stands for OH, chloride, bromide, iodide or cyanide.

3. The process according to claim 1, where the organically soluble quaternary ammonium salt is aliquat 336 (methyl-tri-n-octylammonium chloride).

4. The process according to claim 1, in which the solvent is selected from the group consisting of benzene, toluene, xylene, and mixtures thereof, or the group consisting of hexane, cyclohexane, methylcyclohexane and mixtures thereof.

5. A process for producing a compound of formula (I)

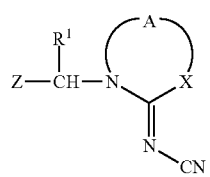

(I)

in which
$R^1$ stands for a hydrogen atom,
A stands for an ethylene group which may be substituted by alkyl, or a trimethylene group which may be substituted by alkyl,
X stands for an oxygen or sulfur atom or the groups

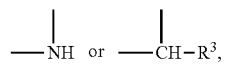

in which
$R^3$ stands for a hydrogen atom or an alkyl group, and
Z is 2-chloro-5-pyridinyl,
said process comprising reacting one or more compounds of formula (II)

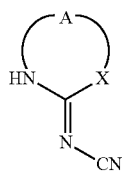

(II)

or salts thereof of formula (IIa),

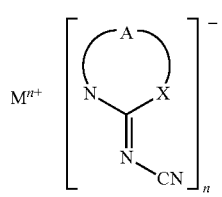

(IIa)

in which
A and X are as defined above,
depending on the counterion ($M^{n+}$) n may be one or two,
$M^{n+}$ represents ammonium (n=1), alkali metal (n=1) or alkaline earth metal cation (n=2),
in a nonpolar aliphatic or aromatic organic solvent in the presence of a phase transfer catalyst,
with 2-chloro-5-chloromethylpyridine,
wherein the solvent is toluene.

6. The process according to claim 1, wherein $M^+$ is an $Na^+$ ion.

7. The process for producing a compound of formula (I) according to claim 1, wherein the compound of formula (I) is the compound of formula (Ia)

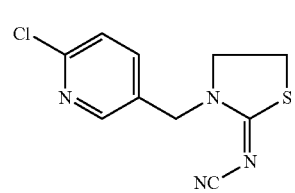

(Ia)

said process comprising reacting one or more compounds of formula (IIb)

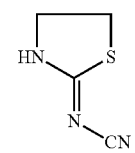

(IIb)

in the presence of a base,
or salts thereof of formula IIc,

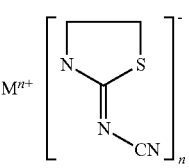

(IIc)

wherein depending on the counterion $M^{n+}$ n is one or two and $M^{n+}$ is an ammonium (n=1), an alkali metal (n=1) or an alkaline earth metal cation (n=2), in the presence of said phase transfer catalyst
with 2-chloro-5-chloromethylpyridine.

8. The process according to claim 1, wherein the alkyl group in R and A is a $C_1$-$C_4$-alkyl group.

9. The process according to claim 1, wherein the phase transfer catalyst is an ammonium salt.

10. The process according to claim 1, wherein the phase transfer catalyst is a quaternary ammonium salt.

11. The process according to claim 2, wherein $R_7$ stands for a $C_1$-$C_{12}$-alkyl group, and anion⁻ stands for chloride.

12. The process according to claim 1, wherein the solvent is selected from the group consisting of benzene, toluene, xylene, and mixtures thereof.

13. The process according to claim 7, wherein the base is NaOH, and $M^{n+}$ is a $Na^{+\ ion}$.

* * * * *